(12) United States Patent
Hong et al.

(10) Patent No.: US 7,223,824 B2
(45) Date of Patent: May 29, 2007

(54) MULTINUCLEAR TRANSITION METAL COMPOUND AND CATALYST SYSTEM INCLUDING THE SAME

(75) Inventors: Sah-Mun Hong, Daejeon (KR); Sung-Woo Kang, Daejeon (KR); Young-Jae Jun, Daejeon (KR); Jin-Sook Oh, Daejeon (KR); Hyun-Ki Yoon, Daejeon (KR)

(73) Assignee: Daelim Industrial Co., Ltd., Seoul (KR)

( * ) Notice: Subject to any disclaimer, the term of this patent is extended or adjusted under 35 U.S.C. 154(b) by 0 days.

(21) Appl. No.: 11/169,895

(22) Filed: Jun. 30, 2005

(65) Prior Publication Data

US 2006/0004155 A1 Jan. 5, 2006

(30) Foreign Application Priority Data

Jul. 1, 2004 (KR) .................. 10-2004-0051206

(51) Int. Cl.
*C08F 4/52* (2006.01)
*C08F 4/76* (2006.01)

(52) U.S. Cl. .................. 526/113; 526/114; 526/115; 526/116; 526/117; 526/170; 526/160; 526/943; 502/103; 556/53

(58) Field of Classification Search .............. 526/113, 526/116, 115, 117, 170, 943, 160, 114; 502/103; 556/53
See application file for complete search history.

(56) References Cited

U.S. PATENT DOCUMENTS

| | | | |
|---|---|---|---|
| 4,530,914 A | 7/1985 | Ewen et al. | |
| 4,874,880 A | 10/1989 | Miya et al. | |
| 4,975,403 A | 12/1990 | Ewen | |
| 5,324,800 A | 6/1994 | Welborn, Jr. et al. | |
| 5,442,020 A | 8/1995 | Davis | |
| 5,585,508 A | 12/1996 | Kuber et al. | |
| 5,627,117 A | 5/1997 | Mukaiyama et al. | |
| 5,753,577 A | 5/1998 | Hamura et al. | |
| 5,780,659 A | 7/1998 | Schmid et al. | |
| 5,830,958 A | 11/1998 | Peifer et al. | |
| 5,880,302 A * | 3/1999 | Herrmann et al. | ............ 556/28 |
| 5,892,079 A | 4/1999 | Wilson, Jr. | |
| 5,962,359 A | 10/1999 | Aulbach et al. | |
| 5,986,024 A | 11/1999 | Wilson, Jr. | |
| 6,010,974 A | 1/2000 | Kim et al. | |
| 6,262,197 B1 | 7/2001 | Aulbach et al. | |
| 6,344,528 B1 | 2/2002 | Ushioda et al. | |
| 6,414,162 B1 * | 7/2002 | Nagy | .................. 548/406 |
| 6,642,400 B2 | 11/2003 | Holtcamp et al. | |
| 2004/0072677 A1 | 4/2004 | Lee et al. | |

FOREIGN PATENT DOCUMENTS

| | | |
|---|---|---|
| DE | 2608933 A1 | 9/1977 |
| DE | 3007725 A1 | 9/1981 |
| DE | 4312270 A1 | 10/1994 |
| EP | 0129368 B1 | 7/1989 |
| JP | 2004-143334 * | 5/2004 |
| KP | 10-0455713 | 6/2004 |

OTHER PUBLICATIONS

Heinemann et al. Organometallics 996, 15, 5462-5463.*
Seki et al. (JP 2004-143334 abstract and translation in English).*
Dalton, J. Amer. Chem. Soc., (1981), pp. 805-813.
Ewen, J.A., J. Amer. Chem. Soc., 106, (1984), pp. 6355-6364.
Kaminsky, W. et al., Makromol. Chem. Rapid Commun., 4, (1983), pp. 417-421.
Manriquez, J. M. et al, J. Amer. Chem. Soc., 100:10, (1978), pp. 3078-3083.

* cited by examiner

*Primary Examiner*—David W. Wu
*Assistant Examiner*—Rip A. Lee
(74) *Attorney, Agent, or Firm*—Birch, Stewart, Kolasch & Birch, LLP

(57) ABSTRACT

A multinuclear transition metal compound which has two or more catalytic active sites, and is useful in preparing the olefin polymer and copolymer, is disclosed. The multinuclear transition metal compound for olefin polymerization includes two or more metals, and at least one ligand having a cyclopentadienyl moiety, which connects the two or more metals. The preferable multinuclear transition metal catalyst for olefin polymerization includes the first transition metal, the first η ligand having a cyclopentadienyl moiety, which is coordinated to the first transition metal, and the second transition metal to which the second η ligand having a cyclopentadienyl moiety is coordinated, wherein the second transition metal is bonded to the first η-ligand via a sigma (σ) bond.

9 Claims, No Drawings

MULTINUCLEAR TRANSITION METAL COMPOUND AND CATALYST SYSTEM INCLUDING THE SAME

FIELD OF THE INVENTION

This invention relates to a multinuclear metal compound, and more particularly to a multinuclear transition metal compound which has two or more catalytic active sites, and is useful in polymerizing olefin polymer and copolymer, a catalyst system including the same, and olefin polymerization process using the same.

BACKGROUNDS OF THE INVENTION

Catalyst including transition metal has been widely used for olefin polymerization. For example, German Patent Nos. 2,608,933 and 3,007,725 have disclosed that metallocene compound consisting of Group 4 transition metal such as zirconium, titanium or hafnium, and a ligand having cyclopentadienyl structure can be used as a catalyst for olefin polymerization in the presence of an activator such as methylaluminoxane. Examples of the ligands include substituted or unsubstituted cyclopentadiene, indene, and fluorene. Various metallocene compounds have been developed to prepare catalyst systems for the olefin polymerization. It has also been known that changes of chemical structures of the metallocene compounds may have significant effects on the suitabilites of the compounds as catalyst. For example, activities, stereospecificities, and stabilities of the catalyst and physical properties of the polymer obtained by the polymerization depend on the sizes and positions of substituents bonded to cyclopentadienyl ligands. Specific examples of the meallocene compounds include bis(alkyl-cyclopentadienyl)zircornium dichloride (wherein, alkyl represents methyl, ethyl, isopropyl, tert-butyl or trimethylsilyl.) [J. Chem. Soc. Dalton Trans., 805(1981)], bis(pentamethyl-cyclopentadienyl)zirconium dichloride [J. Amer, Chm. Soc., 100, 3078(1978)], (pentamethylcyclopentadienyl) (cyclopentadienyl)zirconium dichloride [J. Amer, Chm. Soc., 106, 6355(1984)], bis(di, tri, or tetra alkyl-cyclopentadienyl) zirconium dichloride [U.S. Pat. No. 4,874,880], non-bridged metallocene compounds having substituted indenyl ligands [U.S. Pat. No. 5,780,659], metallocene compounds having mono substituted cyclopentadienyl ligand [German Patent No. 4,312,270], and so on. Recently, it have been discovered that the catalyst system including the metallocene compound, which uses zirconium as the transition metal, and methyl aluminoxane (MAO) activator has high activities in olefin polymerization (European Patent No. 129,368, U.S. Pat. Nos. 4,874,880, and 5,324,800, and Makromol. Chem. Rapid Commun., 4, 417(1983) et al.).

When the catalyst system including only one kind of the metallocene is used for the olefin polymerization, the produced polyolefin has a good mechanical strength and transparency due to the narrow molecular weight distribution (Mw/Mn) of about 2. But the produced polyolefin is not suitable for processing, and the surface of the processed product is not desirable in quality. To improve the physical properties and processability of the produced polyolefin, U.S. Pat. Nos. 4,530,914 and 4,975,403 disclosed a method of preparing polyolefin having wide molecular weight distribution by using two or more metallocenes and cocatalyst. In this method, polyolefins of different properties are produced at the same time due to the different properties of the metallocenes. However, in the method, the reaction conditions are complicated, the control of the molecular weight distribution is difficult, and the reaction conditions should be very carefully controlled to obtain polyolefin having the desirable molecular weight distribution.

Generally, the catalyst system including aluminoxane or organic boron compound and metallocene compound shows best catalytic activity at the polymerization temperature of 60 to 80° C. However, the activity of the catalyst system decreases as the reaction time passes at such a high temperature, and, therefore, the polymerization productivity decreases, the physical properties of the produced polymer are deteriorated, and the produced polymer is not suitable for processing. If the polymerization temperature decreases, the molecular weight of the produced polymer can be increased, but the activity of the catalyst decreases.

In order to solve these problems and to increase the molecular weight distribution of the produced polyolefin, various metallocene catalysts including two or more metals have been developed. For example, U.S. Pat. No. 5,753,577 disclosed a multinuclear metallocene compound including two Group 4 transition metals having oxidation state of 3, in which the two transition metals are directly bonded, and the ligands of the two transition metals are also directly bonded. However, the polymer produced with this multinuclear metallocene catalyst is not satisfactory due to the limitation of its molecular weight. U.S. Pat. No. 5,442,020 disclosed a multinuclear metallocene compound which is produced by reacting Group 4 transition metal compounds and cyclopentadienyls which are connected with alkylene or silylene, and the multinuclear metallocene compound is used for ethylene polymerization, propylene polymerization, and ethylene/$\alpha$-olefin copolymerization. However, the alkylene or silylene group should be used for preparing the catalyst, and therefore, the method of preparing the catalyst is complicated. U.S. Pat. No. 5,627,117 disclosed a multinuclear metallocene compound which is produced by reacting Group 4 to Group 8 transition metal compounds and cyclopentadienyls which are connected with alkylene, silylene, or divalent Ge or Sn, and the multinuclear metallocene compound is used for ethylene polymerization, propylene polymerization, and ethylene/$\alpha$-olefin copolymerization. However, the metallocene compound is not satisfactory due to the low activity at high temperature. U.S. Pat. No. 6,010,974 disclosed a multinuclear metallocene compound which is produced by reacting Group 4 transition metal compounds and cyclopentadienyls which are connected with alkylene or silylene, and the multinuclear metallocene compound is used for styrene polymerization. However, the metallocene compound is not satisfactory since the compound is suitable only for polymerization of styrene. Besides, various multinuclear metallocene catalysts are disclosed in U.S. Pat. Nos. 5,585,508, 5,830,958, 5,892,079, 5,962,359, 5,986,024, 6,262,197, 6,344,528, and 6,642,400, and Korean Laid-Open Patent 2002-0063506 (Application No. 10-2002-0004142).

SUMMARY OF THE INVENTION

Therefore, it is an object of the present invention to provide a multinuclear transition metal compound for olefin polymerization which has desirable activity and stability at high polymerization temperature.

It is other object of the present invention to provide a multinuclear transition metal compound for olefin polymerization which is capable of producing polyolefin having various molecular weights and molecular weight distributions, and good morphology and processibility.

It is another object of the present invention to provide a multinuclear transition metal compound for olefin polymerization which is capable of easily controlling the molecular weights and molecular weight distributions of the produced polyolefin in homogeneous polymerization (solution polymerization) condition and/or heterogeneous polymerization (gas-phase or slurry-phase polymerization) condition.

It is yet another object of the present invention to provide a catalyst system including the multinuclear metal compound, and olefin polymerization method using the same.

To accomplish these and other objects, the present invention provides a multinuclear transition metal compound for olefin polymerization including two or more metals, and at least one ligand having a cyclopentadienyl moiety, which connects the two or more metals. The preferable multinuclear metal catalyst for olefin polymerization includes the first transition metal, the first η ligand having a cyclopentadienyl moiety, which is coordinated to the first transition metal, and the second transition metal to which the second η ligand having a cyclopentadienyl moiety is coordinated, wherein the second transition metal is bonded to the first η ligand via a sigma(σ) bond. If desired, the third transition metal, to which the third η ligand having a cyclopentadienyl moiety is coordinated, can be bonded to the first and/or the second η ligands via a sigma(σ) bond. The present invention also provides a multinuclear metal catalyst system including the multinuclear metal compound and an activator, and a method of polymerizing olefin using the same.

DETAILED DESCRIPTION OF THE INVENTION

A more complete appreciation of the invention, and many of the attendant advantages thereof, will be better appreciated by reference to the following detailed description.

The multinuclear transition metal compound for olefin polymerization according to the present invention includes two or more metals, and at least one ligand having a cyclopentadienyl moiety, which connects the two or more metals. The metals can be independently selected from the group consisiting of transition metals of Group 3 to Group 12 of the Periodic Table, metals of Lanthanide Series, and metals of Actinide Series, and the preferable metals can be independently selected from titanium, zirconium and hafnium. The ligand having a cyclopentadienyl moiety can be a substituted or unsubstituted cyclopentadienyl, a substituted or unsubstituted indenyl, or a substituted or unsubstituted fluorenyl. The preferable multinuclear metal catalyst for olefin polymerization includes the first transition metal, the first η ligand having a cyclopentadienyl moiety, which is coordinated to the first transition metal, and the second transition metal to which the second η ligand having a cyclopentadienyl moiety is coordinated, wherein the second transition metal is bonded to the first η ligand via a sigma(σ) bond. The preferable multinuclear transition metal catalyst can includes several metals in a manner that the third transition metal, to which the third η ligand having a cyclopentadienyl moiety is coordinated, is successively bonded to the first and/or the second η ligands via a sigma(σ) bond.

The more preferable examples of the multinuclear transition metal compound for olefin polymerization include the compounds of the following Formulas 1 to 4.

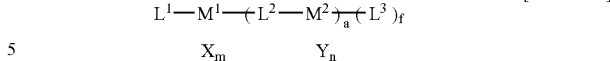

[Formula 1]

In Formula 1, $M^1$ and $M^2$ are independently selected from the group consisiting of transition metals of Group 3 to Group 12 of the Periodic Table, metals of Lanthanide Series, and metals of Actinide Series, preferably are independently selected from transition metals of Group 4, Group 5 and Group 6 of the Periodic Table, more preferably are independently selected from transition metals of Group 4 of the Periodic Table, and most preferably are zirconium, hafnium or titanium; $L^1$, $L^2$ and $L^3$ are independently a ligand having a cyclopentadienyl moiety (for example, cyclopentadienyl, indenyl or fluorenyl), or a ligand having a substituted cyclopentadienyl moiety having at least one substituents selected from the group consisisting of alkyl of 1 to 20 carbon atoms, cycloalkyl of 3 to 20 carbon atoms, alkylsilyl of 1 to 20 carbon atoms, alkylstannyl of 1 to 20 carbon atoms, alkylplumbyl of 1 to 20 carbon atoms, haloalkyl of 1 to 20 carbon atoms, aryl of 6 to 20 carbon atoms, arylalkyl of 6 to 20 carbon atoms, arylsilyl of 6 to 20 carbon atoms, alkylaryl of 6 to 20 carbon atoms, alkoxy of 1 to 20 carbon atoms, alkylsiloxy of 1 to 20 carbon atoms, aryloxy of 6 to 20 carbon atoms, halogen atom and amino group; X and Y are independently a leaving group, preferably an anionic leaving group, and more preferably the $L^1$, $L^2$, $L^3$, hydrogen, hydrocarbyl (for example, alkyl of 1 to 20 carbon atoms, cycloalkyl of 3 to 20 carbon atoms, haloalkyl of 1 to 20 carbon atoms, aryl of 6 to 20 carbon atoms, arylalkyl of 6 to 20 carbon atoms, alkylaryl of 6 to 20 carbon atoms), alkylsilyl of 1 to 20 carbon atoms, arylsilyl of 6 to 20 carbon atoms, alkylstannyl of 1 to 20 carbon atoms, alkylplumbyl of 1 to 20 carbon atoms, alkoxy of 1 to 20 carbon atoms, alkylsiloxy of 1 to 20 carbon atoms, aryloxy of 6 to 20 carbon atoms, halogen atom, amino, or tetrahydroborate; a is an integer of 1 to 5; f is 0 or 1; m and n are an integer of 1 to 5, which is determined according to the oxidation number of the metal. In Formula 1, sigma(σ) bond can be formed between $M^2$ and a carbon atom of $L^2$ ligand, and pi(π) bonds can be formed between $L^1$ and $M^1$, between $L^2$ and $M^1$, and between $M^2$ and $L^3$.

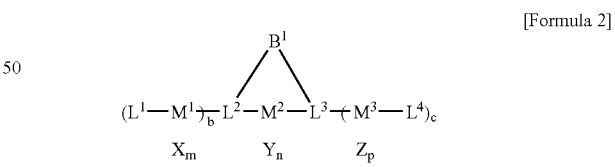

[Formula 2]

In Formula 2, $M^1$, $M^2$ and $M^3$ are independently as defined for $M^1$ of Formula 1; $L^1$, $L^2$, $L^3$, and $L^4$ are independently as defined for $L^1$ of Formula 1; X, Y and Z are independently as defined for X of Formula 1; $B^1$ is a bridging group for bridging ligands $L^2$ and $L^3$, and is a connecting group or a single group selected from the group consisting of alkylene, substituted alkylene, silylene, substituted silylene, a group containing divalent tin, and a group containing divalent germanium; b and c are independently an integer of 0 to 5, and b+c is equal to or more than 1; m, n and p are independently an integer of 1 to 5, which is determined according to the oxidation number of the metal.

Preferably, sigma(σ) bonds can be formed between $M^1$ and a carbon atom of $L^2$ ligand, and between $M^3$ and a carbon atom of $L^3$ ligand, and pi(π) bonds can be formed between $L^1$ and $M^1$, between $L^2$ and $M^2$, between $M^2$ and $L^3$, and between $M^3$ and $L^4$.

[Formula 3]

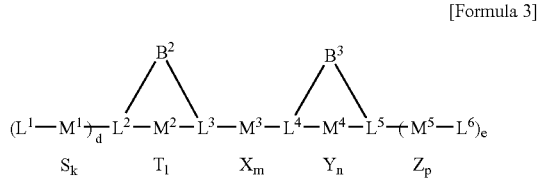

In Formula 3, $M^1$ to $M^5$ are independently as defined for $M^1$ of Formula 1; $L^1$ to $L^6$ are independently as defined for $L^1$ of Formula 1; S, T, X, Y and Z are independently as defined for X of Formula 1; $B^2$ and $B^3$ are respectively a bridging group for bridging ligands $L^2$ and $L^3$, and ligands $L^4$ and $L^5$, and are independently as defined for $B^1$ of Formula 2; d and e are independently an integer of 0 to 5; k, l, m, n and p are independently an integer of 1 to 5, which is determined according to the oxidation number of the metal. Preferably, sigma(σ) bonds can be formed between $M^1$ and a carbon atom of $L^2$ ligand, between $M^3$ and a carbon atom of $L^3$ ligand, between $M^3$ and a carbon atom of $L^4$ ligand, and between $M^5$ and a carbon atom of $L^5$ ligand, and pi(π) bonds can be formed between $L^1$ and $M^1$, between $L^2$ and $M^2$, between $M^2$ and $L^3$, between $L^4$ and $M^4$, between $M^4$ and $L^5$, and between $M^5$ and $L^6$.

[Formula 4]

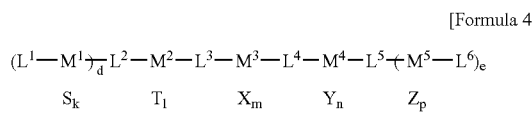

In Formula 4, $M^1$ to $M^5$ are independently as defined for $M^1$ of Formula 1; $L^1$ to $L^6$ are independently as defined for $L^1$ of Formula 1; S, T, X, Y and Z are independently as defined for X of Formula 1; d and e are independently an integer of 0 to 5; k, l, m, n and p are independently an integer of 1 to 5, which is determined according to the oxidation number of the metal. Preferably, sigma(σ) bonds can be formed between $M^1$ and a carbon atom of $L^2$ ligand, between $M^3$ and a carbon atom of $L^3$ ligand, between $M^3$ and a carbon atom of $L^4$ ligand, and between $M^5$ and a carbon atom of $L^5$ ligand, and pi(π) bonds can be formed between $L^1$ and $M^1$, between $L^2$ and $M^2$, between $M^2$ and $L^3$, between $L^4$ and $M^4$, between $M^4$ and $L^5$, and between $M^5$ and $L^6$.

The more preferable multinuclear transition metal compound for olefin polymerization of the present invention includes the compound of Formula 5, in which a of Formula 1 is 1, the compound of Formula 6, in which b of Formula 2 is 1, c of Formula 2 is 0, and the compound of Formula 7, in which both of b and c of Formula 2 are 1.

[Formula 5]

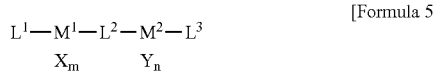

In Formula 5, $M^1$, $M^2$, $L^1$, $L^2$, $L^3$, X, Y, m and n are as defined for Formula 1. Preferably, in Formula 5, sigma(σ) bond can be formed between M2 and a carbon atom of $L^2$ ligand, and pi(π) bonds can be formed between $L^1$ and $M^1$, and between $M^2$ and $L^3$.

[Formula 6]

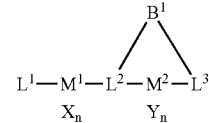

[Formula 7]

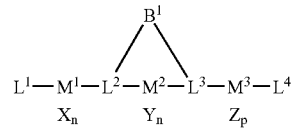

In Formulas 6 and 7, $M^1$, $M^2$, $M^3$, $L^1$, $L^2$, $L^3$, $L^4$, X, Y, Z, $B^1$, m, n and p are as defined for Formula 2. Preferably, in Formulas 6 or 7, sigma(σ) bond can be formed between $M^1$ and a carbon atom of $L^2$ ligand, and between $M^3$ and a carbon atom of $L^3$ ligand, and pi(π) bonds can be formed between $L^1$ and $M^1$, between $L^2$ and $M^2$, between $M^2$ and $L^3$, and between $M^3$ and $L^4$.

Other preferable multinuclear transition metal compound for olefin polymerization of the present invention includes the compound of Formula 8, in which both of d and e of Formula 3 are 0, the compound of Formula 9, in which d of Formula 3 is 1 and e of Formula 3 is 0, and the compound of Formula 10, in which both of d and e of Formula 3 are 1.

[Formula 8]

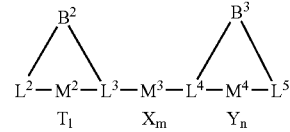

[Formula 9]

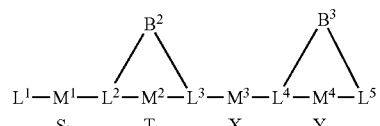

[Formula 10]

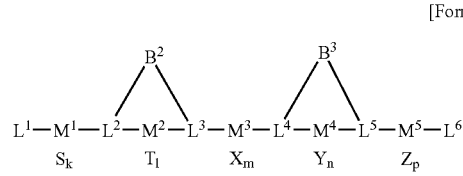

In Formula 8, 9 and 10, $M^1$, $M^2$, $M^3$, $M^4$, $M^5$, $L^1$, $L^2$, $L^3$, $L^4$, $L^5$, $L^6$, S, T, X, Y, Z, $B^2$, $B^3$, k, l, m, n and p are as defined for Formula 3. Preferably, in Formulas 8–10, sigma(σ) bonds can be formed between $M^1$ and a carbon atom of $L^2$ ligand, between $M^3$ and a carbon atom of $L^3$ ligand, between $M^3$ and a carbon atom of $L^4$ ligand, and between $M^5$ and a carbon atom of $L^5$ ligand, and pi(π) bonds can be formed between $L^1$ and $M^1$, between $L^2$ and $M^2$, between $M^2$ and $L^3$, between $L^4$ and $M^4$, between $M^4$ and $L^5$, and between $M^5$ and $L^6$.

Another preferable multinuclear transition metal compound for olefin polymerization of the present invention includes the compound of Formula 11, in which both of d and e of Formula 4 are 0, the compound of Formula 12, in which d of Formula 4 is 1 and e of Formula 4 is 0, and the compound of Formula 13, in which both of d and e of Formula 4 are 1.

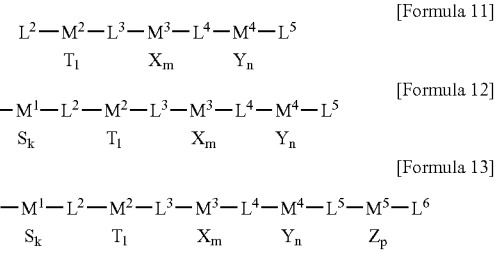

In Formula 11, 12 and 13, $M^1$, $M^2$, $M^3$, $M^4$, $M^5$, $L^1$, $L^2$, $L^3$, $L^4$, $L^5$, $L^6$, S, T, X, Y, Z, k, l, m, n and p are as defined for Formula 4. Preferably, in Formulas 11–13, sigma($\sigma$) bonds can be formed between $M^1$ and a carbon atom of $L^2$ ligand, between $M^3$ and a carbon atom of $L^3$ ligand, between $M^3$ and a carbon atom of $L^4$ ligand, and between $M^5$ and a carbon atom of $L^5$ ligand, and pi($\pi$) bonds can be formed between $L^1$ and $M^1$, between $L^2$ and $M^2$, between $M^2$ and $L^3$, between $L^4$ and $M^4$, between $M^4$ and $L^5$, and between $M^5$ and $L^6$.

As the metal for $M^1$, $M^2$, $M^3$, $M^4$ or $M^5$, the transition metals of Group 4 of the Periodic Table can be preferably used, and zirconium, hafnium or titanium can be more preferably used. The non-limiting examples of the ligand having a cyclopentadienyl moiety ($L^1$ to $L^6$) include alkyl substituted cyclopentadienyl, such as cyclopentadienyl, methylcyclopentadienyl, dimethylcyclopentadienyl, trimethylcyclopentadienyl, tetramethylcyclopentadienyl, ethylcyclopentadienyl, diethylcyclopentadienyl, triethylcyclopentadienyl, n-propylcyclopentadienyl, i-propylcyclopentadienyl, n-butylcyclopentadienyl, i-butylcyclopentadienyl, t-butylcyclopentadieny, or so on; alkyl substituted indenyl, such as indenyl, 2-methylindenyl, 3-methylindenyl, dimethylindenyl, trimethylindenyl, 2-ethylindenyl, 3-ethylindenyl, diethylindenyl, 2-phenylindenyl, 3-phenylindenyl, triethylindenyl, or so on; and fluorenyl or alkyl substituted fluorenyl group.

The non-limiting examples of the substituent which can be substituted to the ligand having a cyclopentadienyl moiety ($L^1$ to $L^6$) includes normal or branched alkyl of 1 to 20 carbon atoms, such as methyl, ethyl, propyl, isopropyl, butyl, isobutyl, tertiarybutyl, pentyl, isopentyl, tertiarypentyl, hexyl, isohexyl, octyl, nonyl, dodecyl, eicosyl, or so on; cycloalkyl of 3 to 20 carbon atoms, such as cyclopropyl, cyclobutyl, cyclopentyl, cyclohexyl, norbonyl, adamantyl, or so on; alkenyl, such as vinyl, propenyl, hexenyl, cyclohexenyl, or so on; alkylsilyl of 1 to 20 carbon atoms, such as methylsilyl, dimethylsilyl, trimethylsilyl, ethylsilyl, diethylsilyl, triethylsilyl, propylsilyl, dipropylsilyl, tripropylsilyl, butylsilyl, dibutylsilyl, tributylsilyl, or so on; alkylstannyl of 1 to 20 carbon atoms, such as methylstannyl, dimethylstannyl, trimethylstannyl, ethylstannyl, diethylstannyl, triethylstannyl, propylstannyl, dipropylstannyl, tripropylstannyl, butylstannyl, dibutylstannyl, tributylstannyl, or so on; alkylplumbyl group of 1 to 20 carbon atoms, such as methylplumbyl, dimethylplumbyl, trimethylplumbyl, ethylplumbyl, diethylplumbyl, triethylplumbyl, propylplumbyl, dipropylplumbyl, tripropylplumbyl, butylplumbyl, dibutylplumbyl, tributylplumbyl, or so on; haloalkyl of 1 to 20 carbon atoms 1 to 20, such as trifluoro methyl; aryl of 6 to 20 carbon atoms, such as phenyl, biphenyl, terphenyl, naphthyl, fluorenyl, benzyl, phenanthryl, or so on; arylalkyl of 6 to 20 carbon atoms, such as phenylethyl, phenylpropyl, or so on; arylsilyl of 6 to 20 carbon atoms, such as phenylsilyl, phenyldimethylsilyl, diphenylmethylsilyl, triphenylsilyl, or so on; alkylaryl of 6 to 20 carbon atoms, such as methylphenyl, dimethylphenyl, trimethylphenyl, ethylphenyl, diethylphenyl, triethylphenyl, propylphenyl, dipropylphenyl, tripropylphenyl, or so on; alkoxy of 1 to 20 carbon atoms, such as methoxy, ethoxy, propoxy, butoxy, pentoxy, hexyloxy, or so on; alkylsiloxy of 1 to 20 carbon atoms, such as methylsiloxy, dimethylsiloxy, trimethylsiloxy, ethylsiloxy, diethylsiloxy, triethylsiloxy, or so on; aryloxy of 6 to 20 carbon atoms, such as phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy, or so on; halogen atom; amino, such as dimethylamino, diethylamino, dipropylamino, dibutylamino, diphenylamino, dibenzylamino, or so on. In addition, when two or more substituents are substituted to the cyclopentadienyl moiety, the two or more substituents can be bonded to form a ring.

Examples of the leaving group (S, T, X, Y and Z) of the multinuclear transition metal compound include the ligand having a cyclopentadienyl moiety ($L^1$ to $L^6$), hydrocarbyl of 1 to 20 carbon atoms, aryloxy of 6 to 20 carbon atoms, and halogen atom. Preferably, at least one of the leaving group is alkyl substituted cyclopentadienyl, such as cyclopentadienyl, methylcyclopentadienyl, dimethylcyclopentadienyl, trimethylcyclopentadienyl, tetramethylcyclopentadienyl, pentamethylcyclopentadienyl, ethylcyclopentadienyl, diethylcyclopentadienyl, triethylcyclopentadienyl, n-propylcyclopentadienyl, i-propylcyclopentadienyl, n-butylcyclopentadienyl, i-butylcyclopentadienyl, t-butylcyclopentadienyl, or so on; alkyl substituted indenyl, such as indenyl, 2-methylindenyl, 3-methylindenyl, dimethylindenyl, trimethylindenyl, 2-ethylindenyl, 3-ethylindenyl, diethylindenyl, 2-phenylindenyl, 3-phenylindenyl, triethylindenyl, or so on; fluorenyl or alkyl substituted fluorenyl; aryloxy, such as phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy; ethylene, acetylene, butadiene; nitrogen containing group, such as —$N(C_2H_5)_3$, —$N(C_2H_5)_2$, pyrrole, pyridine, or so on; oxygen containing group, such as —$OCH_3$, —O-tert-$C_4H_9$, —OPh, —OCOPh, —$C(O)CH_3$, or so on, wherein "Ph" is phenyl; silicon containing group, such as —$OSi(CH_3)_2$, —$CH_2Si(CH_3)_3$, or so on; phosphorus containing group, such as —$P(CH_3)_3$, —$P(C_4H_9)_3$, —PPh, —P$(CH_2)_2$Ph, —$P(CH_3)Ph_2$, —$P(O-C_2H_5)_3$, —P(O-iso-$C_3H_7)_3$, or so on; sulfur containing group, such as —$OSO_2PhCH_3$, —$OSO_2CF_3$, or so on; halogen atom, such as fluorine atom, chlorine atom, bromine atom or iodine atom. The number of halogen which is bonded to the central metal depends on the oxidation state of the metal. The leaving group (S, T, X, Y, and Z) can be the same or different, even though the leaving group is expressed with same reference character, such as S, T, X, Y, or Z. The above k, l, m, n and p are independently an integer of 1 to 5, which depends on the oxidation state (namely, oxidation number) of the central metal, and preferably an integer of 1 to 3.

The bridging group ($B^1$, $B^2$ and $B^3$) of the multinuclear metal compound is a connecting group or a single group selected from the group consisting of alkylene, substituted alkylene, silylene, substituted silylene, a group containing divalent tin, and a group containing divalent germanium, and, if necessary, the connecting group may contain one or more hetero atoms, such as oxygen, nitrogen, sulfur, phosphorus, or so on. Examples of the bridging group includes alkylene, such as methylene, dimethylmethylene, diethylmethylene, ethylene, methylethylene, dimethylethylene, trimethylethylene, tetramethylethylene, tetraethylethylene, propylene, butylene, cyclohexylene, or so on; substituted alkylene, such as diphenylmethylene, tetraphenylethylene, tetrafluoroethylene, isopropylidene, or so on; substituted silylene, such as dimethylsilylene, diethylsilylene, diphenylsilylene, methylphenylsilylene, dimethylsilylene, diethylsilylene, methylphenylsilylene, or so on; a group containing divalent tin, in which the silicon of the substituted silylene is replaced with tin; and a group containing divalent germanium, in which the silicon of the substituted silylene is replaced with germanium. The preferable examples of the bridging group includes alkylene, substituted alkylene, silylene, substituted silylene and the group containing divalent germanium.

The specific examples of the multinuclear transition metal compound for olefin polymerization according to the present invention include the following compounds, wherein $M^1$ to $M^5$ are independently as defined for $M^1$ of Formula 1; S, T, X, Y and Z are independently as defined for X of Formula 1.

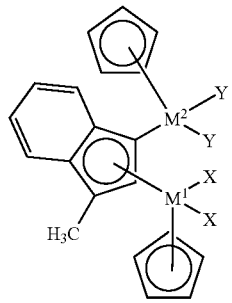
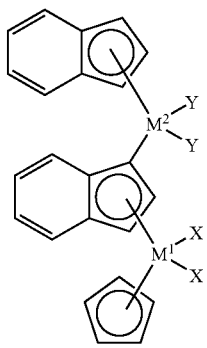
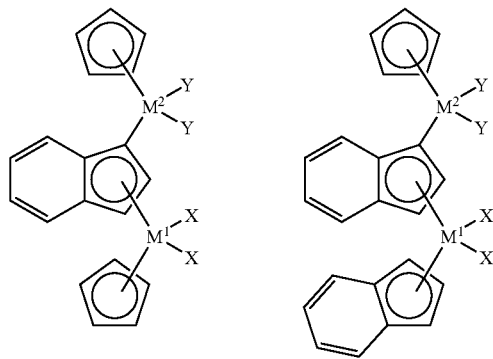
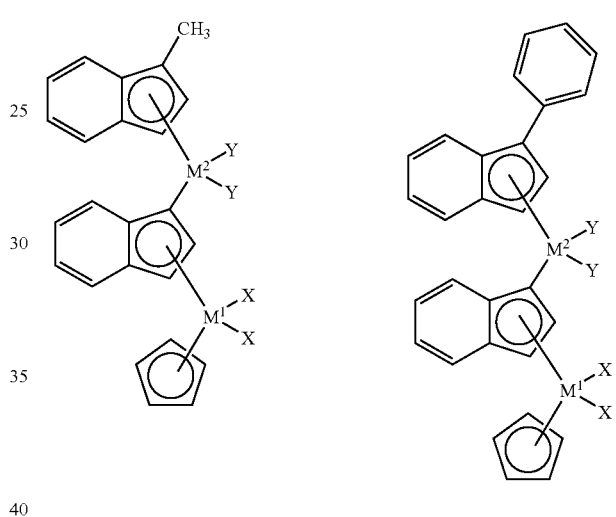
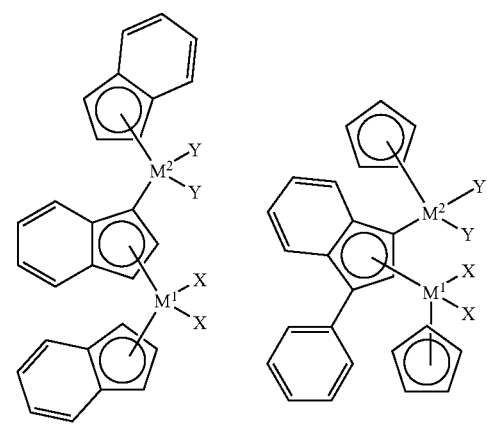
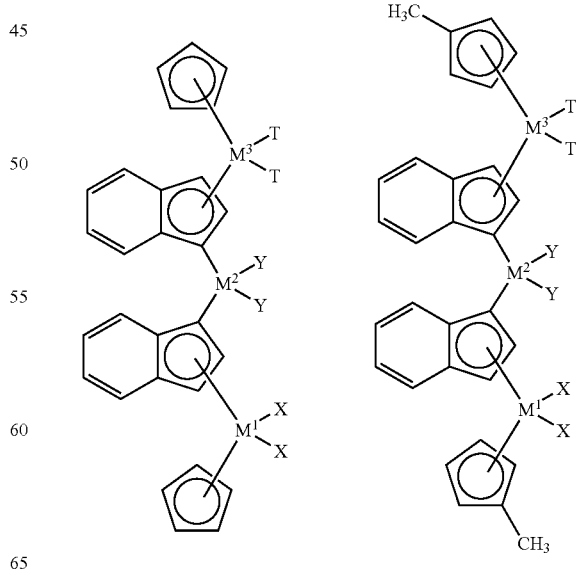

-continued

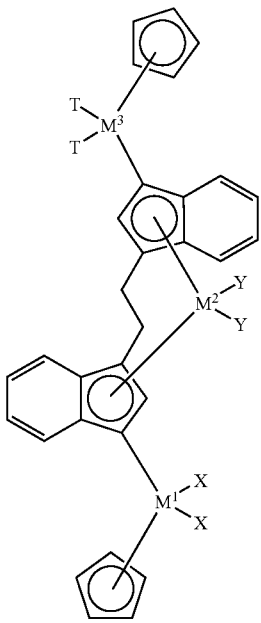

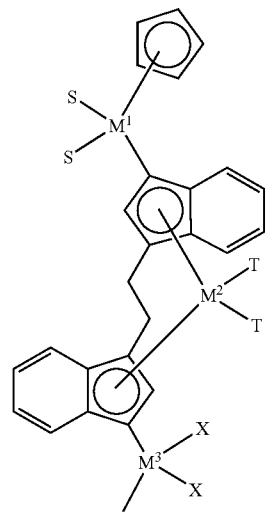

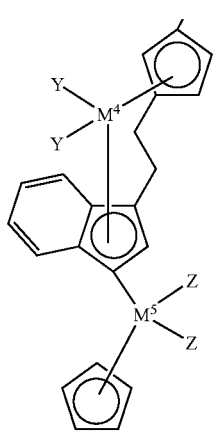

-continued

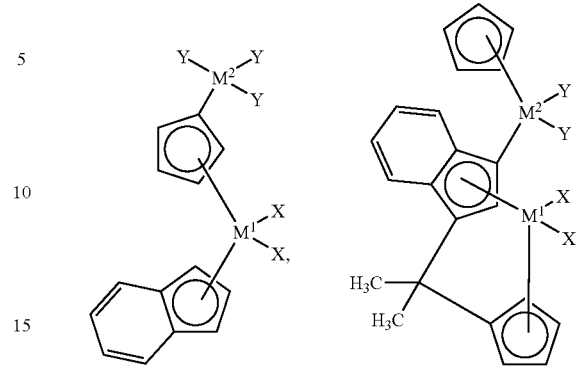

Hereinafter, examples of the method for preparing the multinuclear transition metal compound for olefin polymerization according to the present invention will be explained. For example, as shown in Reaction 1, the compound of Formula 1 can be prepared by reacting the compound of Formula 14 and the compound of Formula 15 in a solvent.

[Formula 14]
$$L^1\text{—}M^1\text{—}L^2ER'_3$$
$$X_m$$

[Formula 15]
$$L^3\text{—}M^2$$
$$Y_nY'$$

[Reaction 1]
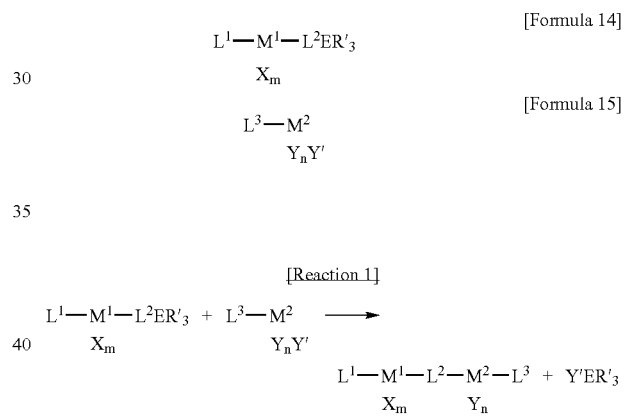

In Formula 14, 15 and Reaction 1, $M^1$, $M^2$, $L^1$, $L^2$, $L^3$, X, Y, m and n are as defined for Formula 1; Y' can be a halogen atom, such as fluorine atom, chlorine atom, bromine atom or iodine atom; $ER'_3$ is an organic metalloid substituted with hydrocarbyl group, and preferably is trimethylstannyl [—Sn(CH$_3$)$_3$], triethylstannyl [—Sn(C$_2$H$_5$)$_3$], tripropylstannyl [—Sn(n-C$_3$H$_7$)$_3$], tributylstannyl [—Sn(n-C$_4$H$_9$)$_3$], trimethylplumbyl [—Pb(CH$_3$)$_3$], triethylplumbyl [—Pb(C$_2$H$_5$)$_3$], tripropylplumbyl [—Pb(n-C$_3$H$_7$)$_3$], or tributylplumbyl [—Pb(n-C$_4$H$_9$)$_3$]. The above reaction can be carried out at the temperature of 60 to 100° C. for 8 hours to 2 days in the presence of of a solvent. The preferable solvent for this reaction includes methylenedichloride, toluene, xylene, and so on. Preferably, the reaction product can be purified by the processes, such as solvent removal, filtration, recrystallization, and/or sublimation.

As other example, as shown in Reaction 2, the compound of Formula 14 can be prepared by reacting the compound of Formula 16 and the compound of Formula 17 in a solvent.

[Formula 16]

$$L^1—M^1$$
$$X_mX'$$

[Formula 17]

$$L^2(ER'_3)_2$$

[Reaction 2]

$$L1—L1\ M1 + L2(ER'3)2 \longrightarrow$$
$$X_mX'$$

$$L1—M1—L2ER'3 + X'ER'3$$
$$X_m$$

In Formula 16, 17 and Reaction 2, $M^1$, $L^1$, $L^2$, X and m n are as defined for Formula 1, X' can be a halogen atom, such as fluorine atom, chlorine atom, bromine atom or iodine atom, $ER'_3$ is as defined for Formula 14. The above reaction can be carried out at the temperature of 20 to 100° C. for 8 hours to 2 days in the presence of of a solvent. The preferable solvent for this reaction includes methylenedichloride, toluene, xylene, and so on. Preferably, the reaction product can be purified by the processes, such as solvent removal, filtration, recrystallization, and/or sublimation.

The compound of Formula 4 can be prepared by reacting 2 equivalents of the compound of Formula 14 and the compound of Formula 18 in a solvent, which is shown in Reaction 3.

$$M^2Y_nY'_2$$ [Formula 18]

[Reaction 3]

$$2L^1—M^1—L^2ER'_3 + M^2Y_nY'_2 \longrightarrow (L^1—M^1—L^2)_2—M^2$$
$$X_m \qquad\qquad\qquad\qquad X_m \quad Y_n$$

In Formula 18 and Reaction 3, $M^1$, $M^2$, $L^1$, $L^2$, X, Y, m and n are as defined for Formula 1, Y' can be a halogen atom, such as fluorine atom, chlorine atom, bromine atom or iodine atom, $ER'_3$ is as defined for Formula 14.

As an example of the method for preparing the multi-nuclear transition metal compound of the present invention, the compound of Formula 2 can be prepared by reacting the compound of Formula 19 and the compound of Formula 20-1 in a solvent, which is shown in Reaction 4.

[Formula 19]

$$L^1—M^1$$
$$X_mX'$$

[Formula 20-1]

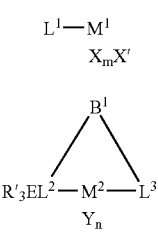

[Formula 20-2]

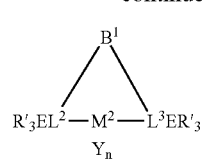

[Reaction 4]

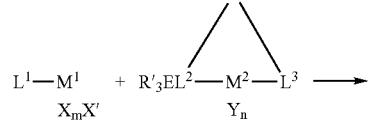

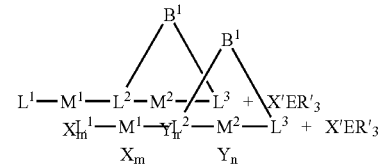

In Formulas 19, 20-1 and Reaction 4, $M^1$, $M^2$, $B^1$, $L^1$, $L^2$, $L^3$, X, Y, m and n are as defined for Formula 2, X' can be a halogen atom, such as fluorine atom, chlorine atom, bromine atom or iodine atom, $ER'_3$ is as defined for Formula 14.

As other example of the method for preparing the multi-nuclear transition metal compound of the present invention, the compound of Formula 2 can be prepared by reacting the compound of Formula 19 and the compound of Formula 20-2 in a solvent, which is shown in Reaction 5.

[Reaction 5]

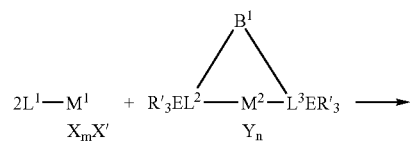

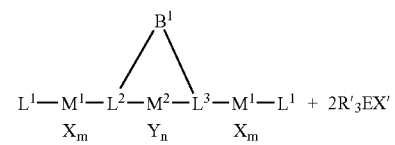

In Reaction 5, $M^1$, $M^2$, $B^1$, $L^1$, $L^2$, $L^3$, X, Y, m and n are as defined for Formula 2, X' can be a halogen atom, such as fluorine atom, chlorine atom, bromine atom or iodine atom, $ER'_3$ is as defined for Formula 14.

The activator, which is an ingredient of the multinuclear transition metal catalyst system of the present invention, activates the multinuclear metal compound. Exemplary activator includes alkyl aluminoxane, organic aluminium compound, bulky aromatic fluoride compound, modified clay, Lewis acid inorganic oxide, and the mixtures thereof. The alkyl aluminoxane can be represented by the following Formula 21, and may have linear, cyclic, or network structure. The alkyl aluminoxane is commercially available, and the non-limiting examples thereof include linear or cyclic oligomeric hydrocarbyl aluminoxanes of Formula 22 and 23. The more specific examples of the alkyl aluminoxane include methylaluminoxane (MAO), ethylaluminoxane, butylaluminoxane, hexylaluminoxane, octylaluminoxane and decylaluminoxane. As the aluminoxane, commercially available aluminoxane dissolved in hydrocarbon solution is preferable, aluminoxane dissolved in aromatic hydrocarbon solution is more preferable, and aluminoxane dissolved in toluene is most preferable. Single aluminoxane or mixture of various aluminoxanes can be used for the present invention.

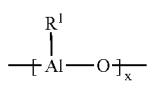
[Formula 21]

In Formula 21, $R^1$ is a hydrocarbyl radical of 1 to 10 carbon atoms, and x is an integer of 1 to 70.

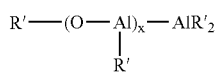
[Formula 22]

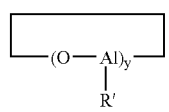
[Formula 23]

In Formulas 22 and 23, R' can be the same or different, and is a hydrocarbyl radical, preferabley a linear or branched alkyl radical of 1 to 10 carbon atoms, and more preferably methyl; x is an integer of 1 to 50, and preferably an integer of 10 to 40; y is an integer of 3 to 50, and preferably an integer of 10 to 40. The alkyl aluminoxane can be prepared by various conventional methods, and, for example, can be prepared by adding proper amount of water to trialkylaluminium, or, by reacting hydrocarbyl compound with water or inorganic hydrated salt with trialkylaluminium. In general, a mixture of linear aluminoxane and cyclic aluminoxane is obtained.

In the catalyst system of the present invention, the organic aluminium compound of Formula 24 can be used.

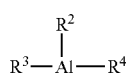
[Formula 24]

In Formula 24, $R^2$, $R^3$ and $R^4$ are independently alkyl of 1 to 10 carbon atoms, alkoxy of 1 to 10 carbon atoms or halide, and at least one of $R^2$, $R^3$ and $R^4$ is alkyl. The non-limiting examples of the organic aluminium compound include trialkylaluminium, such as trimethylaluminium, triethylaluminium, tributylaluminium, trihexylaluminium, trioctylaluminium, tridecylaluminium, or so on; dialkylaluminium alkoxide, such as dimethylaluminium methoxide, diethylaluminium methoxide, dibutylaluminium methoxide, or so on; dialkylaluminium halide, such as dimethylaluminium chloride, diethylaluminium chloride, dibutylaluminium chloride, or so on; alkylaluminium dialkoxide, such as methylaluminium dimethoxide, ethylaluminium dimethoxide, butylaluminium dimethoxide, or so on; alkylaluminium dihalide, such as methylaluminium dichloride, ethylaluminium dichloride, butylaluminium dichloride, or so on.

As another activators, the fluoride substituted bulky aromatic compound can be represented by Formula 25.

[C][D]     [Formula 25]

In Formula 25, C is a cation, which is combined hydrogen ion to a Lewis base, or metal or non-metal having an oxidation power, and D is a compound including an element of Group 5 to Group 15 of the Periodic Table and an organic substance. The non-limiting examples of the bulky aromatic fluoride compound include trimethylammonium tetrakis (pentafluorophenyl)borate, triethylammonium tetrakis(pentafluorophenyl)borate, tripropylammonium tetrakis (pentafluorophenyl)borate, tributylammonium tetrakis (pentafluorophenyl)borate, anilinium tetrakis (pentafluorophenyl)borate, pyridinium tetrakis (pentafluorophenyl)borate, ferrocenium tetrakis (pentafluorophenyl)borate, silver tetrakis (pentafluorophenyl)borate, tris(pentafluorophenyl)borane, tris(3,4,5-trifluorophenyl)borane, and so on. Among the activators, the exemplary modified clay includes N,N-dimethylanilinium montmorillonite, N,N-dimethylanilinium hectorite, and so on, and the other exemplary activator is a Lewis acid inorganic oxide, such as, fluorinated silica alumina.

The transition metal compound and the activator constituting the multinuclear transition metal catalyst system of the present invention can be used for olefin polymerization in a solution condition, in which the transition metal compound and the activator are dissolved in a hydrocarbon solvent, or can be used for gas-phase or slurry-phase olefin polymerization in solid or insoluble particle state, in which the metallocene compound and the activator are impregnated in a support. As the porous support for impregnating the multinuclear metal compound and the activator, stable porous inorganic compound, inorganic salt, or organic compound having micro pores on the surface thereof and large surface area can be used without limitations. The non-limiting examples of the inorganic materials includes silica, alumina, bauxite, zeolite, $MgCl_2$, $CaCl_2$, MgO, $ZrO_2$, $TiO_2$, $B_2O_3$, CaO, ZnO, BaO, $ThO_2$, and mixtures thereof, such as $SiO_2$—MgO, $SiO_2$—$Al_2O_3$, $SiO_2$—$TiO_2$, $SiO_2$—$V_2O_5$, $SiO_2$—$Cr_2O_3$, $SiO_2$—$TiO_2$—MgO, and so on, and the above mentioned compounds including small amount of carbonate, sulfate, or nitrate. The non-limiting examples of the organic support include starch, cyclodextrine, and synthetic polymer. The solvent useful in supporting the catalyst of the present invention into a support includes aliphatic hydrocarbon solvent, such as pentane, hexane, heptane, octane, nonane, decane, undecane, doidecane, or so on; aromtic hydrocarbon solvent, such as benzene, monochlorobenzene, dichlorobenzene, trichlorobenzene, toluene, or so on; and halogenated aliphatic hydrocarbon solvent, such as dichloromethane, trichloromethane, dichloroethane, trichloroethane, or so on. The solvent or the mixtures thereof can be used for the supporting process.

The amount of the multinuclear transition metal compound (A), and the amount of the organic aluminoxane compound (B), organic aluminium compound (B) or bulky compound (B) for activating the metal compound can be varied in wide range. However, the mole ratio of metals in the supported system (B)/(A), namely, [aluminium]/[transition metal] is preferably 1/1 to 104/1, and more preferably 1/1 to $5 \times 10^2/1$. When the bulky fluoride substituted aromatic compound (B) is an organic boron compound, the mole ratio of the organic boron compound (B) and the multinuclear transition metalcompound (A) ([organic boron compound]/[transition metal compound]) is generally 1 to 1,000, and preferably 1 to 100. The temperature for catalyst supporting process is preferably 0~120° C., and more preferably 0~90° C.

When performing olefin polymerization with the catalyst of the present invention, the multinuclear transition metal compound and the activator can be used in a solution state, in which the multinuclear transition metal compound and the activator are uniformly dissolved in a solvent, or the multinuclear metal compound and the activator can be used in a supported state or insoluble particle state, in which the metallocene compound and the activator are supported in an inorganic support (for example, silica, alumina, silica-alumina mixture, or so on). The present invention is not limited to the types of the polymerization methods. Therefore, the catalyst of the present invention for olefin polymerization can be used for solution phase, slurry phase, bulk phase or gas phase polymerization. The conditions for the polymerization reactions can be varied according to the type of the metal catalyst, the state of the metal catalyst/activator (homogeneous uniform or heterogeneous phase (supported phase)), polymerization method (solution polymerization, slurry polymerization, gas phase polymerization), or desired polymer properties.

When the polymerization is carried out in solution phase or slurry phase, a solvent or olefin, which is a reactant, can be used as the reaction medium. Exemplary solvent includes propane, butane, pentane, hexane, octane, decane, dodecane, cyclopentane, methylcyclopentane, cyclohexane, benzene, toluene, xylene, dichloromethane, chloroethane, 1,2-dichloroethane, chlorobenzene, and so on, and, if desired, mixtures of the solvents can be used. The catalyst of the present invention can be used for homo polymerization of monomer, or can be used for copolymerization of monomer and comonomer. The suitable olefin for the polymerization or copolymerization is aliphatic olefin monomer of 2 to 10 carbon atoms. Preferable monomer incudes α-olefin of 2 to 20 carbon atoms, such as ethylene, propylene, butene-1, pentene-1, 3-methylbutene-1, hexene-1, 4-methylpentene-1, 3-methylpentene-1, heptene-1, octene-1, decene-1, 4,4-dimethyl-1-pentene, 4,4-diethyl-1-hexene, 3,4-dimethyl-1-hexene, or so on; diolefin of 4 to 20 carbon atoms, such as 1,3-butadiene, 1,4-pentadiene, 2-methyl-1,3-butadiene, or so on; cycloolefin or cyclodiolefin of 3 to 20 carbon atoms, such as cyclopentene, cyclohexene, cyclopentadiene, cyclohexadiene, norbornene, methyl-2-norbonene, or so on; and styrene or substituted styrene substituted with alkyl of 1 to 10 carbon atoms, alkoxy of 1 to 10 carbon atoms, halogen, amine, silyl, halogenated alkyl, or so on.

For the polymerization of the olefin with the catalyst of the present invention, the amount of the transition metal compound (A) can be varied in wide range. However, the preferable concentration of the metal is $10^{-8}$ to 10 mol/l in the polymerization reaction system, and the more preferable concentration is $10^{-7}$ to $10^{-2}$ mol/l. The temperature of the polymerization can also be varied in wide range according to the reactant(s), reaction conditions, or so on. When performing the solution polymerization, the temperature of the polymerization is generally 0 to 250° C., and more preferably 10 to 200° C. When performing the gas phase polymerization, the temperature of the polymerization is generally 0 to 120° C., and more preferably 20 to 100° C. The pressure for the polymerization reaction is generally atmospheric pressure to 500 kg/cm², and more preferably atmospheric pressure to 50 kg/cm². The polymerization reaction can be carried out in batch type, semi-continuous type, or continuous type. In addition, the polymerization can be carried out by two or more steps of different reaction conditions. The molecular weight of the polymer produced with the catalyst of the present invention can be controlled by changing the polymerization temperature, or by injecting hydrogen into the polymerization reactor.

The catalyst of the present invention can be used for pre-polymerization of one or more olefins. In pre-polymerization, the amount of the produced polymer is preferably 0.05 to 500 g, more preferably 0.1 to 300 g, and most preferably 0.2 to 100 g with respect to 1 g of the catalyst. The olefin for the pre-polymerization includes α-olefin of 2 to 20 carbon atoms, such as ethylene, propylene, 1-butene, 1-pentene, 4-methyl-1-pentene, 1-hexene, 1-octene, 1-decene, 1-dodecene, 1-tetradecene, 3-methyl-1-butene, 3-methyl-1-pentene, or so on, and the more suitable olefin for the pre-polymerization is the same olefin which will be used in the main polymerization.

Hereinafter, the preferable examples are provided for better understanding of the present invention. However, the present invention is not limited to the following examples. In the following examples, the multinuclear transitiom metal compound was obtained by Schlenk method under blocking air and water. And purified and dried nitrogen was used as an inert gas. Also, solvent was dried under existing inert nitrogen atmosphere and sodium metal, dichloromethane was dried under existing calcium hydride. Deuterated solvent for nuclear magnetic resonance spectroscopy was stored in a molecular sieve and used. Melt Index (MI) and HLMI (high load Melt Index) of polymer were measured in accordance with ASTM D1238, and density of polymer was measured in accordance with ASTM D1505.

EXPERIMENTAL EXAMPLE 1

Preparation of Multinuclear Transition Metal Compound (A)

After adding diethylaminotrimetylstanne (33.48 g, 141.9 mmol), indene (8.23 g, 70.86 mmol) and THF (20 ml) into a 500 mL flask under nitrogen atmosphere, and the mixture solution was refluxed by heating for 17 hours. Volatile of the obtained mixture was removed under vacuum, and as colorless liquid materials, bis(trimethylstannyl)indene of 16.42 g was obtained by distillation under reduced pressure.

Cyclopentadienylzirconium trichloride ($CpZrCl_3$, 3.94 g, 15.0 mmol) which was slurrified by adding toluene of 70 ml was added into the mixed solution including bis(trimethylstannyl)indene (6.75 g, 15.28 mmol) and toluene of 100 ml, and then reacted for 21 hours at 85° C. Yellowish (trimethylstannyl-indenyl)(cyclopentadienyl)zirconium dichloride compound (6.71 g, yield: 86%) was obtained by a series of processes, such as removing toluene from reactant, slurrifying the obtained solid by adding hexane (100 ml) and filtering the slurry.

Two kinds of toluene mixtures were prepared by the following method. Toluene (50 ml) was added into the obtained (trimethylstannyl-indenyl)(cyclopentadienyl) zirconium dichloride compound (3.06 g, 6.24 mmol) and toluene (50 ml) was added into cyclopentadienyl zirconium trichloride (1.64 g, 6.24 mmol). Above mentioned two kind of toluene mixtures were mixed and reacted at 85° C. for 24 hours. Bright yellowish solid powder, multinuclear transition metal compound (3.16 g, yield: 89%) was obtained by a series of processes, such as removing toluene from the obtained mixture, extracting resultant by methylenedichloride, filtering the solution, removing volatile from filtrate, slurrifying the solid by adding hexane (100 ml) and filtering the slurry mixture. Spectroscopic analysis by the NMR method is as follows: $^1$H NMR (CDCl$_3$): 7.78–7.75(m, 2H), 7.25–7.43(m, 2H), 7.14(d, 1H), 6.79(s, 5H), 6.08(s, 5H).

EXPERIMENTAL EXAMPLE 2

Preparation of Multinuclear Transition Metal Compound (B)

After adding litiumidenide (IndLi) powder (17.52 g, 0.144 mol) and hexane (300 ml) into a 500 mL flask under nitrogen atmosphere, tributyltin chloride (41 ml, 0.145 mol) was injected into the above mentioned flask with syringe slowly. The mixture is stirred at room temperature for 48 hours. Yellowish oil type product was obtained by a series of processes, such as separating the organic liquid by filtering reaction mixture and removing volatile from filtrate. Then the obtained yellowish oil type product was diluted with methylenedichloride (200 ml), and zirconium tetrachloride (ZrCl4, 33.03 g, 0.142 mol) was added. The mixture is stirred at room temperature for 48 hours. Indenylzirconium trichloride (IndZrCl3, 39.5 g, yield: 88%) was obtained by a series of processes, such as removing the volatile from reaction mixture, slurrifying by adding hexane (200 ml), filtering, collecting scarlet colored solid powder and drying.

Two kinds of toluene mixtures were prepared by the following method. Toluene of 50 ml was added into the obtained indenylzirconium trichloride (IndZrCl$_3$) compound (1.3 g, 4.156 mmol) and toluene (50 ml) was added into (trimethylstannyl-indenyl) (cyclopentadienyl)zirconium dichloride compound (2.1 g, 4.157 mmol). Above mentioned two kind of toluene mixtures were mixed and reacted at 85° C. for 24 hours. Solid powder, multinuclear transition metal compound (2.1 g, yield: 82%) was obtained by a series of processes, such as removing toluene from the reactant mixture, extracting the resultant with methylenedichloride, filtering the liquid, removing volatile from the filtrate, slurrifying the solid by adding hexane (100 ml) and filtering the slurry. Spectroscopic analysis by the NMR method is as follows: $^1$H NMR (CDCl$_3$): 7.79–7.71(m, 4H), 7.25–7.43 (m, 4H), 7.14(d, 2H), 6.83~6.84(d, 1H), 6.79~6.80(d, 1H), 6.08(s, 5H).

EXPERIMENTAL EXAMPLE 3

Preparation of Multinuclear Transition Metal Compound (C)

After adding cyclopntadiene (3.8 ml, 40.85 mmol) into diethylaminotrimethylstanne (20.7 g, 87.73 mmol), the reaction was performed at 40° C. for 3 hours. Colorless liquid, bis(trimethylstannyl)cyclopentadiene was obtained by installing the vacuum distillation system, removing volatile under vacuum, increasing the temperature of the oil bath, and doing vacuum distillation under reduced pressure. Bis (trimethylstannyl)cyclopentadiene (4.39 g, 11.21 mmol) was diluted with toluene (80 ml), then IndZrCl$_3$ (3.5 g, 11.19 mmol) mixture was added. The reaction was performed in the oil bath at 85° C. for 21 hours (clear yellow solution). Yellowish compound, [Trimethylstannylcyclopentadienyl] (Indenyl)ZrCl$_2$](4.18 g, yield: 74%) was obtained by a series of processes, such as removing toluene and volatile under vacuum, dissolving by adding methylene chloride (50 ml), filtering the liquid, removing volatile again, slurrifying by adding hexane (100 ml), filtering, collecting solid powder, and drying with vacuum.

The obtained [(trimethylstannylcyclopentadienyl)(Indenyl)ZrCl$_2$]](1.522 g, 3.013 mmol) and IndZrCl$_3$ (0.942 g, 3.012 mmol) were placed in each flask respectively, and toluene (50 ml) was added to each flask. The slurry of IndZrCl3/toluene was added into the flask having (trimethylstannyl cyclopentadienyl)(Indenyl)ZrCl$_2$/toluene. The reaction was performed in the oil bath at 85° C. for 24 hours. Orange colored binuclear transition metal compound (1.69 g, yield: 91%) was obtained by a series of processes, such as filtering the reaction mixture, removing volatile from the filtrate, dissolving by adding methylene chloride (50 ml), evaporating methylene chloride until 30% volume under vacuum, filtering the residue again, collecting solid powder, and drying under vacuum.

EXPERIMENTAL EXAMPLE 4

Preparation of Multinuclear Transition Metal Compound (D)

After adding (trimethylstannylcyclopentadienyl)(indenyl) ZrCl$_2$ (0.468 g, 0.926 mmol) and zirconium tetrachloride (ZrCl$_4$, 0.216 g, 0.926 mmol) into a flask, toluene (80 ml) was added. The reaction was performed in the oil bath at 80 to 90° C. for overnight. Faint ocherous powder was obtained by a series of processes, such as removing toluene, extracting with methylene chloride (80 ml), filtering the liquid, and removing volatile from the filtrate, slurrifying the residue by adding hexane (80 ml) to filtrate.

EXPERIMENTAL EXAMPLE 5

Preparation of Multinuclear Transition Metal Compound (E)

After adding multinuclear transition metal compound (B) (0.493 g, 0.797 mmol), which was obtained in experimental example 2, and lithium-methylcyclopentadienide (0.274 g, 3.18 mmol) into a flask, toluene (100 ml) was added. The reaction was performed in the oil bath at 80 to 90° C. for overnight. Yellow-orange colored powder was obtained by a series of processes, such as: removing toluene with vacuum, extracting with methylene chloride (80 ml), filtering, and removing volatile from the filtrate, slurrifying the residue by adding hexane (80 ml) to filtrate.

EXPERIMENTAL EXAMPLE 6

Preparation of Multinuclear Transition Metal Compound (F)

After adding multinuclear transition metal compound (C) (0.189 g, 0.3 mmol), which was obtained in experimental example 3, and litium methylcyclopentadienide (0.0526 g, 0.6 mmol) into a flask, toluene (50 ml) was added to form suspension. Then the reaction was performed in the oil bath at 80 to 90° C. for overnight. The yellowish solid object was obtained by filtering the reaction mixture and removing toluene from the filtrate with vacuum.

EXPERIMENTAL EXAMPLE 7

Preparation of Supported Catalyst and Polymerization

<Preparation of Supported Catalyst>

After adding methyl aluminoxane (MAO, 10% toluene solution, Al 4.64 wt %) (11.0 mL) into multinuclear transition metal compound (46 mg), which was obtained in experimental example 1, ultrasonic treatment was performed for 1 hours. Then silica (Grace Davison D948) (2.0 g) calcinated at 250° C. was added, and ultrasonic treatment was performed for 1 hours again. A supported catalyst was obtained by a series of processes, such as discarding supernatant, adding hexane (40 ml), washing by shaking for 5 minutes, removing hexane, and drying with vacuum.

<Polymerization>

Stainless autoclave reactor (1L) was washed one time with isobutane and five times with ethylene at 85° C. to remove contaminants in the reactor, and then cooled to 67° C. The reactor was equipped with jacket for supplying cooling water from outside in order to control the polymerization temperature. Isobutane (400 ml) and triethylaluminium (0.5 mmol) were added to the reactor, and then stirred at 75° C. Then, isobutane (100 ml) and multinuclear transition metal compound supported catalyst (43 mg), which was obtained in previous process, were added into the reactor, and then ethylene and 1-hexene (20 ml) was added until the partial pressure of ethylene increased up to 220 psig. The polymerization was performed at 80° C. for 1 hours with maintaining total pressure of reactor to 420 psig. Partial pressure of ethylene was being kept to 220 psig, and 1-hexene was added continuously during polymerization. The amount of 1-hexene was 6 weight % for the amount of the ethylene mass folw, which was measured by Mass Flowmeter. After the completion of polymerization, remained 1-hexene and propane were removed, polymer (125 g) having free flow property was obtained easily from the reactor. There was no observation about a fouling phenomenon. Polymerization activity was 2,200 g polymer/g.catalyst.hours.

EXPERIMENTAL EXAMPLE 8

Preparation of Multinuclear Transition Metal Supported Catalyst and Polymerization <Preparation of Supported Catalyst>

Supported catalyst was obtained by the same method like experimental example 7 except using multinuclear transition metal compound (85 mg), which was obtained in manufacturing example 2, and silica (Ineos ES757) (2.0 g).

<Polymerization>

Polymerization of olefin was performed by the same method like experimental example 7 except using multinuclear transition metal compound supported catalyst (38 mg), which was obtained in above mentioned. Polymerization activity of polyolefin was 3,695 g polymer/g.catalyst.hours, and the obtained polymer had MI of 0.458 g/10 min, HLMI of 7.57 g/10 min, and density of 0.9223 g/cm$^3$.

EXPERIMENTAL EXAMPLE 9

Preparation of Multinuclear Transition Metal Supported Catalyst and Polymerization <Preparation of Supported Catalyst>

Supported catalyst was obtained by the same method like experimental example 7 except using multinuclear transition metal compound (84 mg), which was obtained in manufacturing example 3, and silica (Ineos ES757) (2.0 g).

<Polymerization>

Polymerization of olefin was performed by the same method like experimental example 7 except using multinuclear transition metal compound supported catalyst (40 mg), which was obtained in above mentioned. Polymerization activity of polyolefin was 3,150 g polymer/g.catalyst.hours, and the obtained polymer had MI of 0.447 g/10 min, HLMI of 7.46 g/10 min, and density of 0.9281 g/cm$^3$.

EXPERIMENTAL EXAMPLE 10

Preparation of Multinuclear Transition Metal Supported Catalyst and Polymerization <Preparation of Supported Catalyst>

Supported catalyst was obtained by the same method like experimental example 7 except using multinuclear transition metal compound (73 mg), which was obtained in manufacturing example 4, and silica (Ineos ES757) (2.0 g).

<Polymerization>

Polymerization of olefin was performed by the same method like experimental example 7 except using multinuclear transition metal compound supported catalyst (39 mg), which was obtained in above mentioned. Polymerization activity of polyolefin was 2,580 g polymer/g.catalyst.hours, and the obtained polymer had MI of 0.362 g/10 min, HLMI of 6.19 g/10 min, and density of 0.9305 g/cm$^3$.

EXPERIMENTAL EXAMPLE 11

Preparation of Multinuclear Transition Metal Supported Catalyst and Polymerization <Preparation of Supported Catalyst>

Supported catalyst was obtained by the same method like experimental example 7 except using multinuclear transition metal compound (108 mg), which was obtained in manufacturing example 5, and silica (Ineos ES757) (2.0 g).

<Polymerization>

Polymerization of olefin was performed by the same method like experimental example 7 except using multinuclear transition metal compound supported catalyst (39 mg), which was obtained in above mentioned. Polymerization activity of polyolefin was 3,230 g polymer/g.catalyst.hours, and the obtained polymer had MI of 0.169 g/10 min, HLMI of 4.1 g/10 min, and density of 0.9305 g/cm$^3$.

EXPERIMENTAL EXAMPLE 12

Preparation of Multinuclear Transition Metal Supported Catalyst and Polymerization <Preparation of Supported Catalyst>

Supported catalyst was obtained by the same method like experimental example 7 except using multinuclear transition metal compound (97 mg), which was obtained in manufacturing example 6, and silica (Ineos ES757) (2.0 g).

<Polymerization>

Polymerization of olefin was performed by the same method like experimental example 7 except using multinuclear transition metal compound supported catalyst (39 mg), which was obtained in above mentioned. Polymerization activity of polyolefin was 5,350 g polymer/g.catalyst.hours, and the obtained polymer had MI of 0.381 g/10 min, HLMI of 6.458 g/10 min, and density of 0.9257 g/cm$^3$.

The multinuclear metal compound for olefin polymerization accoirding to the present invention has industrially desirable catalytic activity and stability, and procudes polyolefin having various molecular weights and molecular weight distributions, and superior morphology and processability. The multinuclear metal compound of the present invention can prevent the fouling phenomena in polymerization reactor, and useful in controlling the molecular weights and molecular weight distributions of the produced polyolefin in homogeneous polymerization (solution polymerization) condition and/or in heterogeneous polymerization (gas-phase or slurry-phase polymerization) condition.

The invention claimed is:

1. A multinuclear transition metal compound for olefin polymerization, comprising:

a first transition metal coordinated to a first ligand having a cyclopentadienyl moiety; and a second transition metal to which a second ligand having a cyclopentadienyl moiety is coordinated, wherein the second transition metal is directly bonded to the cyclopentadienyl moiety of the first ligand via a sigma ($\sigma$) bond, wherein each metal is independently selected from the group consisting of transition metals of Group 3 to Group 12 of the Periodic Table, metals of Lanthanide Series, and metals of Actinide Series, and wherein the first transition metal and the second transition metal are connected only by the cyclopentadienyl moiety of the first ligand.

2. The multinuclear transition metal compound according to claim 1, further comprising a third transition metal, to which a third ligand having a cyclopentadienyl moiety is coordinated, that is bonded to the first and/or the second ligands via a sigma($\sigma$) bond.

3. The multinuclear transition metal compound according to claim 1, wherein the ligand having a cyclopentadienyl moiety is selected form the group consisiting of a substituted or unsubstituted cyclopentadienyl, a substituted or unsubstituted indenyl, and a substituted or unsubstituted fluorenyl.

4. The multinuclear transition metal compound according to claim 1, wherein the transition metal compound is selected form the group consisiting of the compounds of the following Formulas 1 to 4:

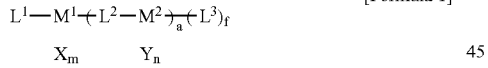

[Formula 1]

In Formula 1, $M^1$ and $M^2$ are independently selected from the group consisting of transition metals of Group 3 to Group 12 of the Periodic Table, metals of Lanthanide Series, and metals of Actinide Series; $L^1$, $L^2$ and $L^3$ are independently a ligand having a cyclopentadienyl moiety or a ligand having a substituted cyclopentadienyl moiety having at least one substituents selected from the group consisting of alkyl of 1 to 20 carbon atoms, cycloalkyl of 3 to 20 carbon atoms, alkylsilyl of 1 to 20 carbon atoms, alkylstannyl of 1 to 20 carbon atoms, alkylplumbyl of 1 to 20 carbon atoms, haloalkyl of 1 to 20 carbon atoms, aryl of 6 to 20 carbon atoms, arylalkyl of 6 to 20 carbon atoms, arylsilyl of 6 to 20 carbon atoms, alkylaryl of 6 to 20 carbon atoms, alkoxy of 1 to 20 carbon atoms, alkylsiloxy of 1 to 20 carbon atoms, aryloxy of 6 to 20 carbon atoms, halogen atom and amino group; X and Y are independently a leaving group; a is an integer of 1 to 5; f is 0 or 1; m and n are an integer of 1 to 5, which is determined according to the oxidation number of the metal;

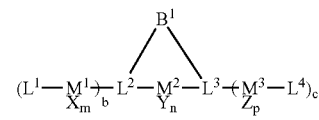

[Formula 2]

In Formula 2, $M^1$, $M^2$ and $M^3$ are independently as defined for $M^1$ of Formula 1; $L^1$, $L^2$, $L^3$, and $L^4$ are independently as defined for $L^1$ of Formula 1; X, Y and Z are independently as defined for X of Formula 1; $B^1$ is a bridging group for bridging ligands $L^2$ and $L^3$, and is a connecting group or a single group selected from the group consisting of alkylene, substituted alkylene, silylene, substituted silylene, a group containing divalent tin, and a group containing divalent germanium; b and c are independently an integer of 0 to 5, and b+c is equal or more than 1; m, n and p are independently an integer of 1 to 5, which is determined according to the oxidation number of the metal;

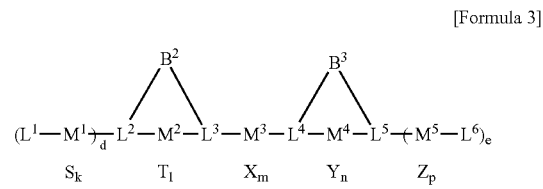

[Formula 3]

In Formula 3, $M^1$ to $M^5$ are independently as defined for M1 of Formula 1; $L^1$ to $L^6$ are independently as defined for $L^1$ of Formula 1; S, T, X, Y and Z are independently as defined for X of Formula 1; $B^2$ and $B^3$ are respectively a bridging group for bridging ligands $L^2$ and $L^3$, and ligands $L^4$ and $L^5$, and are independently as defined for $B^1$ of Formula 2; d and e are independently an integer of 0 to 5; k, l, m, n and p are independently an integer of 1 to 5, which is determined according to the oxidation number of the metal;

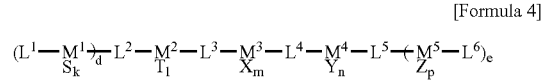

[Formula 4]

In Formula 4, $M^1$ to $M^5$ are independently as defined for $M^1$ of Formula 1; $L^1$ to $L^6$ are independently as defined for $L^1$ of Formula 1; S, T, X, Y and Z are independently as defined for X of Formula 1; d and e are independently an integer of 0 to 5; k, l, m, n and p are independently an integer of 1 to 5, which is determined according to the oxidation number of the metal.

5. A method for preparing a multinuclear transition metal compound for olefin polymerization comprising the step of reacting a compound of Formula 14 and a compound of Formula 15 in a solvent:

[Formula 14]

-continued

   [Formula 15]

in Formula 14, and 15, $M^1$ and $M^2$ are independently selected from the group consisting of transition metals of Group 3 to Group 12 of the Periodic Table, metals of Lanthanide Series, and metals of Actinide Series;

$L^1$, $L^2$ and $L^3$ are independently a ligand having a cyclopentadienyl moiety or a ligand having a substituted cyclopentadienyl moiety having at least one substituent selected from the group consisting of alkyl of 1 to 20 carbon atoms, cycloalkyl of 3 to 20 carbon atoms, alkylsilyl of 1 to 20 carbon atoms, alkyistannyl of 1 to 20 carbon atoms, alkylpiumbyl of 1 to 20 carbon atoms, haloalkyl of 1 to 20 carbon atoms, aryl of 6 to 20 carbon atoms, arylalkyl of 6 to 20 carbon atoms, arylsilyl of 6 to 20 carbon atoms, alkylaryl of 6 to 20 carbon atoms, alkoxy of 1 to 20 carbon atoms, ailcylsiloxy of 1 to 20 carbon atoms, aryloxy of 6 to 20 carbon atoms, halogen atom and amino group;

X and Y are independently a leaving group; a is an integer of 1 to 5; f is 0 or 1;

m and n are an integer of 1 to 5, which is determined according to the oxidation number of the metal;

Y' is a halogen atom; and $ER'_3$ is an organic metalloid substituted with hydrocarbyl group, wherein, in the multinuclear transition metal compound, M1 is coordinated to L2, M2 is coordinated to L3, M2 is directly bonded to the cyclopentadienyl moiety of L2 via a sigma ($\sigma$) bond, and M1 and M2 are connected only by L2.

6. A multinuclear transition metal catalyst system for olefin polymerization, comprising:

a multinuclear transition metal compound comprising: a first transition metal coordinated to a first ligand having a cyclopentadienyl moiety, and a second transition metal to which a second ligand having a cyclopentadienyl moiety is coordinated, wherein the second transition metal is directly bonded to the cyclopentadienyl moiety of the first ligand via a sigma ($\sigma$) bond, wherein each metal is independently selected from the group consisting of transition metals of Group 3 to Group 12 of the Periodic Table, metals of Lanthanide Series, and metals of Actinide Series, and wherein the first transition metal and the second transition metal are connected only by the cyclopentadienyl moiety of the first ligand; and an activator.

7. The multinuclear transition metal catalyst system according to claim 6, wherein the activator is selected from the group consisiting of alkyl aluminoxane, organic aluminium compound, bulky aromatic fluoride compound, modified clay, Lewis acidic inorganic oxide, and the mixtures thereof.

8. The multinuclear transition metal catalyst system according to claim 6, wherein the multinuclear metal compound and the activator are supported on a support.

9. A method of polymerizing olefin, comprising the step of polymerizing olefin in the presence of a catalipt comprising a multinuclear transition metal compound comprising a first transition metal coordinated to a first ligand having a cyclopentadienyl moiety, and a second transition metal to which a second ligand having a cyclopentadienyl moiety is coordinated, wherein the second transition metal is directly bonded to the cyclopentadienyl moiety of the first ligand via a sigma ($\sigma$) bond, wherein each metal is independently selected from the group consisting of transition metals of Group 3 to Group 12 of the Periodic Table, metals of Lanthanide Series, and metals of Actinide Series, and wherein the first transition metal and the second transition metal are connected only by the cyclopentadienyl moiety of the first ligand, by a method selected from the group-consisting of solution phase, slurry phase, bulk phase and gas phase polymerization.

* * * * *